US012642560B1

(12) United States Patent　　　　　　(10) Patent No.:　US 12,642,560 B1
Virupakshappa et al.　　　　　　　　　(45) Date of Patent:　　　Jun. 2, 2026

(54) BONE REPOSITIONING DEVICE AND METHOD OF USE

(71) Applicant: PRINCE SATTAM BIN ABDULAZIZ UNIVERSITY, Al-Kharj (SA)

(72) Inventors: Deepti Virupakshappa, Al-Kharj (SA); Chaitanya Virupakshappa, Davangere (IN); Rajashekhara Bhari Sharanesha, Al-Kharj (SA); Nikethan Bathi, Davangere (IN)

(73) Assignee: PRINCE SATTAM BIN ABDULAZIZ UNIVERSITY, Al-Kharj (SA)

( * ) Notice: Subject to any disclaimer, the term of this patent is extended or adjusted under 35 U.S.C. 154(b) by 0 days.

(21) Appl. No.: 19/412,161

(22) Filed: Dec. 8, 2025

(51) Int. Cl.
　　*A61B 17/66*　　　(2006.01)
　　*A61B 17/62*　　　(2006.01)
(52) U.S. Cl.
　　CPC ................................... *A61B 17/62* (2013.01)
(58) Field of Classification Search
　　CPC ....... A61B 17/62; A61B 17/66; A61B 17/663; A61B 17/666; A61B 17/64; A61B 17/6416; A61B 17/645; A61B 17/6491; A61B 17/7077; A61B 17/6425; A61B 2017/681; A61B 2017/567; A61B 2017/565
　　See application file for complete search history.

(56) References Cited

U.S. PATENT DOCUMENTS

| | | | | |
|---|---|---|---|---|
| 3,941,123 A * | 3/1976 | Volkov | ............... | A61B 17/6425 |
| | | | | 606/56 |
| 6,520,961 B1 * | 2/2003 | Marsh | ..................... | A61F 5/013 |
| | | | | 606/56 |
| 7,621,922 B2 * | 11/2009 | Schendel | ............. | A61B 17/663 |
| | | | | 433/7 |
| 9,289,239 B2 * | 3/2016 | Mingozzi | ........... | A61B 17/6425 |
| 11,166,750 B1 * | 11/2021 | Wurapa | .............. | A61B 17/6416 |
| 12,484,935 B1 * | 12/2025 | Endara | ............... | A61B 17/6475 |

(Continued)

FOREIGN PATENT DOCUMENTS

| | | | | | |
|---|---|---|---|---|---|
| CN | 106725783 A | | 5/2017 | | |
| CN | 107753094 A | * | 3/2018 | ............. | A61B 17/66 |

(Continued)

*Primary Examiner* — Eduardo C Robert
*Assistant Examiner* — Michelle C Green
(74) *Attorney, Agent, or Firm* — Oblon, McClelland, Maier & Neustadt, L.L.P.

(57)　　　　　　ABSTRACT
A bone repositioning device includes a base frame comprising a torus support having a plurality of circular frames. A first armature and a second armature connect to the base frame. The first armature includes a first shaft with a base end and a support end, and a second shaft connected to the first support end. The second armature includes a third shaft with a base end and a support end, and a fourth shaft connected to the second support end. A plurality of dome-shaped pads have a dome side and a contact side configured for attachment to a bone surface. These pads are evenly distributed on the second and fourth shafts, with the shafts passing through the pads. A joint connects the first and second armatures at their respective base ends to the base frame, allowing the armatures three degrees of freedom and movement around the joint.

20 Claims, 5 Drawing Sheets

(56)                 References Cited

U.S. PATENT DOCUMENTS

| | | | | |
|---|---|---|---|---|
| 2006/0229604 A1* | 10/2006 | Olsen | A61B 17/6425 | |
| | | | | 606/54 |
| 2012/0143189 A1* | 6/2012 | Wolfson | A61F 5/013 | |
| | | | | 606/55 |
| 2015/0366587 A1* | 12/2015 | Van Dyke | A61B 17/66 | |
| | | | | 606/57 |
| 2021/0093359 A1* | 4/2021 | Gitlin | A61B 17/6441 | |
| 2022/0346840 A1 | 11/2022 | Langenfeld et al. | | |
| 2024/0156495 A1* | 5/2024 | Zhang | A61B 17/7001 | |

FOREIGN PATENT DOCUMENTS

| | | | | | |
|---|---|---|---|---|---|
| CN | 217040268 U | | 7/2022 | | |
| CN | 222398701 U | * | 1/2025 | | A61B 17/66 |
| EP | 0 832 613 A1 | | 4/1998 | | |

* cited by examiner

BONE REPOSITIONING DEVICE AND METHOD OF USE

STATEMENT OF ACKNOWLEDGMENT

Funding and support provided by Prince Sattam Bin Abdulaziz University, Al-Kharj, Saudia Arabia, through project number PSAU/2025/PT/31900 is gratefully acknowledged.

BACKGROUND

Technical Field

The present disclosure pertains generally to the field of medical devices. More specifically, the present disclosure relates to devices used in dentistry and surgery for the repositioning and stabilization of bones.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

In the fields of dentistry and surgery, procedures involving bone repositioning and stabilization are frequently required for treating conditions such as jaw fractures, defects in the oral cavity, and other facial bone injuries resulting from accidents, trauma, or diseases. Historically, such conditions have been addressed using traditional fixation techniques that may include the use of plates and screws, wires, or external fixators to hold bone structures in place during healing. These methods are established in surgical practice for providing structural support to fractured or repositioned bones.

A number of issues are associated with conventional methods for bone repositioning and stabilization. Traditional techniques often depend on manual manipulation for the alignment of bone fragments, which may result in inaccuracies. Such misalignment can lead to improper healing of the bone, a condition known as malunion, or a complete failure of the bone to heal, known as non-union, potentially causing deformities or functional impairments. In cases involving complex fractures where the bone is broken into multiple pieces, existing devices may not provide sufficient stabilization to prevent shifts or displacement of the bone fragments during the healing process. Furthermore, many existing bone repositioning and stabilization techniques require invasive surgical procedures that involve large incisions, which can lead to significant patient discomfort and long recovery times.

Conventional solutions for bone fixation, such as metal plates, screws, and pins, are widely used to provide structural support to healing bones. These devices are mechanically fastened to the bone to hold fragments in a desired alignment. External fixators are also utilized, where a frame outside the body is attached to the bone with pins or wires. These solutions are designed to immobilize the fracture site to facilitate the natural bone healing process. However, the use of metal plates, screws, and pins can sometimes lead to drawbacks such as tissue irritation, an increased risk of infection at the hardware site, or the necessity for subsequent surgeries to remove the hardware after the bone has fully healed. Such devices may not always conform to the specific anatomical shape of the bone, which could result in patient discomfort. External fixators, while providing stabilization, can be bulky and may affect a patient's ability to perform daily activities, impacting comfort and functional mobility during the recovery period. The outcomes of bone healing can also be inconsistent, varying based on the precision of the initial procedure and the type of fracture being treated.

US20240156495A1 describes a stabilizer assembly for spinal surgery. The stabilizer assembly includes a hinge with rod-bearing leaves and a hinge locking mechanism, and stabilizing rods are coupled to the rod-bearing leaves. The device is configured to prevent compression, distraction, or translation of the spinal cord during a vertebral resection surgery.

CN217040268U describes a shoulder strap spreader for humerus fracture traction. The device comprises a rotating block, threaded rods connected to the rotating block, a sphere with arc-shaped positioning holes, and a rotating shell block. Supporting rods are configured to cooperate with the bottom surface of a scapula for support.

EP0832613A1 describes a multidirectional mandibular distractor. The distractor presents a central portion, two partially threaded straight elements extending from the central portion via spherical articulated joints, and two slides movable axially along the straight elements. The device is fitted to a mandible to adjust pressure for separating bone portions.

CN106725783A describes an elbow joint external fixator. The fixator is composed of a near end needle clamp, a near end retractable rod, an elbow joint hinge, a fine tuning device, a dial, a far end retractable rod, and a far end needle clamp. The structure is designed to achieve concentric traction with the full-motion range of the elbow joint.

US20220346840A1 describes a craniofacial external distraction apparatus. The apparatus may comprise a stationary member configured to be affixed to a head of a patient and laterally disposed distractors that extend inferiorly from the stationary member. The distractors are moveable relative to the stationary member to perform distraction movements in multiple degrees of freedom.

CN222398701U describes a fixing device for femoral fracture. The device includes a fixing band, connecting plates, an adjusting device, and a placement device with a placing ring. A threaded supporting rod is provided to adjust the height and position of an internal supporting rod to maintain the reduction state of a femoral fracture.

Each of the aforementioned references suffers from one or more drawbacks hindering their adoption, such as limitations in providing a stable, multi-point anchoring frame, a lack of integrated multi-shaft armatures for complex three-dimensional adjustments, and the absence of specialized bone-contacting interfaces that distribute force evenly. Accordingly, it is one object of the present disclosure to provide a bone repositioning device that incorporates a stable base frame with adjustable, multi-component armatures and a plurality of specialized pads to enable precise control over bone alignment and offer adaptable stabilization for a variety of fracture types and anatomical locations, thereby addressing the limitations of existing solutions.

SUMMARY

In an aspect, a bone repositioning device is described, comprising a base frame comprising a torus support having a plurality of circular frames on the outer surface of the torus support; a first armature and a second armature connecting to the base frame, wherein the first armature comprises a first shaft having a first base end and a first support end, and a second shaft connecting to the first support end of the first shaft; wherein the second armature comprises a third shaft having a second base end and a second support end, and a fourth shaft connecting to the second support end of the second shaft; and a plurality of dome-shaped pads having a dome side and a contact side, wherein the plurality of dome-shaped pads are configured to attach to a bone surface on the contact side, wherein the plurality of dome-shaped pads are evenly distributed on the second shaft and the fourth shaft, and wherein the second shaft and the fourth shaft pass through the plurality of dome-shaped pads; and a joint connecting the first armature and the second armature at the base end to the base frame, configured to allow the first armature and the second armature to have three degrees of freedom, wherein the first armature and the second armature are configured to move around the joint.

In some embodiments, the joint further comprises a locking system, configured to restrict movement of the first armature and the second armature.

In some embodiments, the first armature and the second armature are configured to have movements in forward, backward, rotational, and vertical direction around the joint.

In some embodiments, the second shaft is configured to rotate around the axis of the first shaft at an angle of 10 to 350 degrees; and wherein the fourth shaft is configured to rotate around the axis of the third shaft an angle of 10 to 350 degrees.

In some embodiments, the second shaft and fourth shaft are configured to have an adjustable length.

In some embodiments, the base frame has a diameter of 0.1 to 10 cm.

In some embodiments, the first shaft and the third shaft each has a length of 0.1 to 15 cm.

In some embodiments, the second shaft and the fourth shaft each has a length of 0.1 to 5 cm, and is capable of extending to a length of 5 to 15 cm.

In some embodiments, each of the plurality of dome-shaped pads has a diameter of 0.05 to 5 cm.

In some embodiments, each of the plurality of dome-shaped pads has a depth of 0.05 to 3 cm.

In some embodiments, the bone repositioning device is made with a biocompatible material selected from the group consisting of a non-biodegradable metallic material, a bio-degradable metallic material, a non-biodegradable polymer, a bio-degradable polymer, a bioceramic material, and combinations thereof.

In some embodiments, the bone repositioning device is made with a biocompatible metallic material selected from the group consisting of titanium, a titanium alloy, stainless steel, a cobalt-chromium alloy, porous tantalum, gold, silver, magnesium, a magnesium alloy, iron, an iron alloy, zinc, a zinc alloys, and combinations thereof.

In some embodiments, the bone repositioning device is made with a biocompatible polymer selected from the group consisting of polylactic acid, polyglycolic acid, polycaprolactone, polyethylene terephthalate, polyurethanes, polyetheretherketone, polyethylene, polytetrafluoroethylene, polystyrene, polycarbonates, collagen, gelatin, chitosan, cellulose, and combinations therefore.

In some embodiments, the bone repositioning device is made with a bioceramic material selected from the group consisting of calcium phosphate cements, hydroxyapatite, tricalcium phosphate, biphasic calcium phosphate, bioactive glass, and combinations thereof.

In some embodiments, the bone repositioning device is made with a biodegradable material having a degradation period of 14 to 1000 days.

In some embodiments, the bone repositioning device is used in at least one bone selected from the group consisting of skull, jaw bone, collar bone, shoulder blade, sternum, humerus, radius, ulna, spine, pelvis, sacrum, femur, patella, tibia, and fibula.

In an aspect, a method of repositioning and healing a bone using the bone reposition device is described, comprising: exposing the repositioning bone area surgically to show a movable bone and an adjacent stable bone; affixing the base frame to the stable bone to anchor the device; adjusting the first and second armatures to the movable bone; attaching the plurality of dome-shaped pads to the movable bone; and locking the joint to hold the bone in place during the healing.

In some embodiments, the method further comprises removing the device after the healing.

In some embodiments, the affixing is achieved using one or more cortical screws.

In some embodiments, the attaching further comprises mounting the plurality of dome-shaped pads to the movable bone with screws, glue, or suction.

The foregoing general description of the illustrative embodiments and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1A:
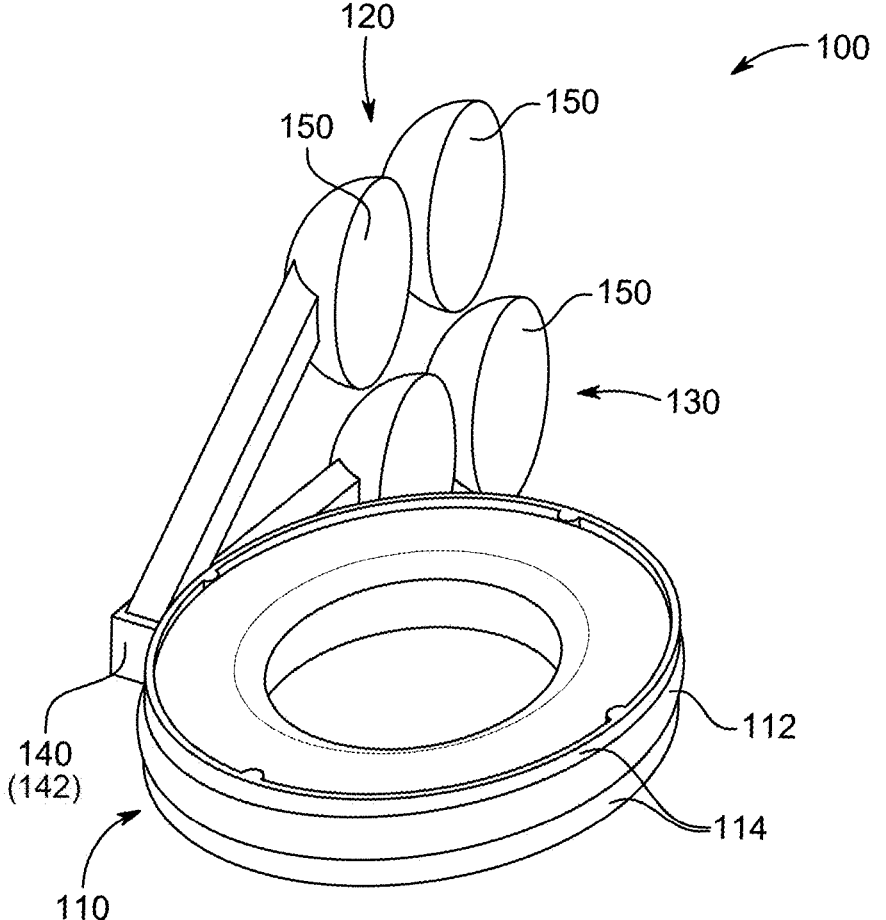
FIG. 1A is a perspective view of a bone repositioning device, according to certain aspects of the present disclosure.

In the drawings, like reference numerals designate identical or corresponding parts throughout the several views. Further, as used herein, the words "a", "an", and the like generally carry a meaning of "one or more", unless stated otherwise.

Furthermore, the terms "approximately," "approximate", "about", and similar terms generally refer to ranges that include the identified value within a margin of 20%, 10%, or preferably 5%, and any values therebetween.

Aspects of this disclosure are directed to a bone repositioning device for the repositioning and healing of a bone and a method of use. The bone repositioning device provides a mechanical system configured for external application to achieve precise alignment and stable fixation of bone segments during surgical procedures. This system is designed to facilitate controlled manipulation of bone fragments, particularly in complex anatomical areas like the craniofacial region, to correct deformities or stabilize fractures.

Referring to FIGS. 1A-1G, various views of a bone repositioning device 100 are illustrated, according to certain aspects of the present disclosure. The bone repositioning device 100 is designed to provide precise control over the alignment of bone fragments and to maintain stabilization during the healing process. The bone repositioning device 100 is configured for external application and can be used for procedures such as craniofacial repositioning, fracture stabilization, or distraction osteogenesis where precise manipulation of bone is required. The bone repositioning device 100 of the present disclosure provides a mechanical system for the precise alignment and stabilization of bone. The bone repositioning device 100 is preferably mounted externally over the human skull (cranial bone). The design of the bone repositioning device 100 integrates mechanical principles to allow for fine-tuned adjustments in multiple spatial dimensions, providing surgeons with a high degree of control during surgical procedures.

The bone repositioning device 100 is configured with multiple interconnected components, including a structural base, adjustable linkages, and bone-interfacing elements. As shown in the perspective view of FIG. 1A, the bone repositioning device 100 includes as its main assemblies a base frame 110, a first armature 120, a second armature 130, a joint 140, and dome-shaped pads 150, e.g., the dome shaped pads may be spherical segments, oval segments, spherical wedges, oval wedge segments, and the like. These assemblies are interconnected to facilitate the repositioning and stabilization of a movable bone segment relative to a stable bone structure. The multi-component configuration is intended for application in various medical scenarios, including the treatment of complex fractures and corrective osteotomies, where accurate repositioning of bone segments is required for functional recovery.

Figure 1B:
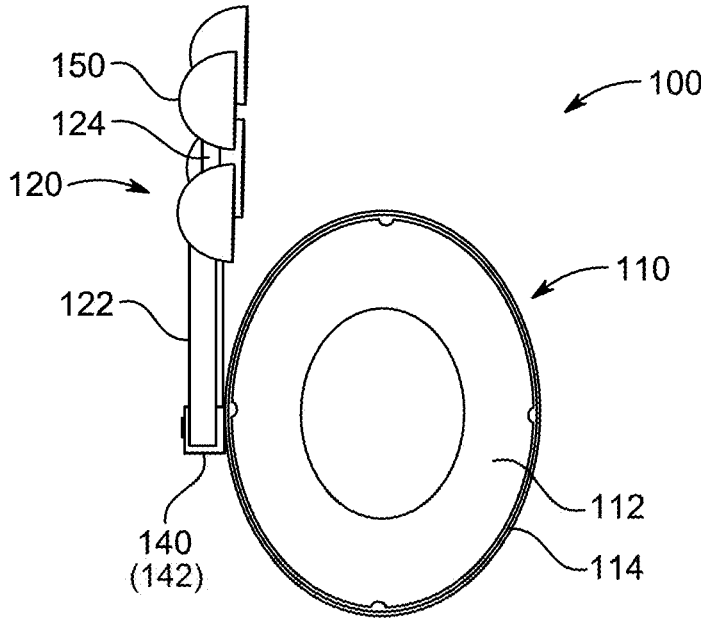
FIG. 1B is a top view of the bone repositioning device shown in FIG. 1A, according to certain aspects of the present disclosure.
Figure 1C:
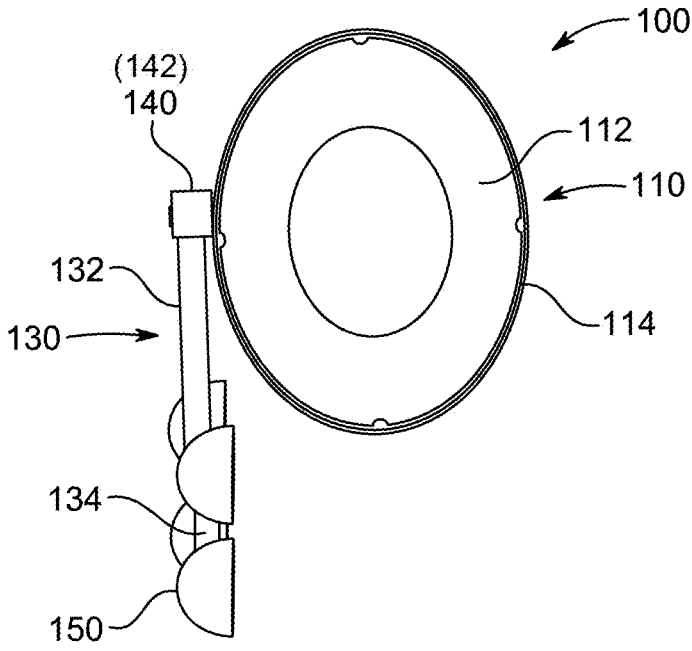
FIG. 1C is a bottom view of the bone repositioning device shown in FIG. 1A, according to certain aspects of the present disclosure.
Figure 1D:
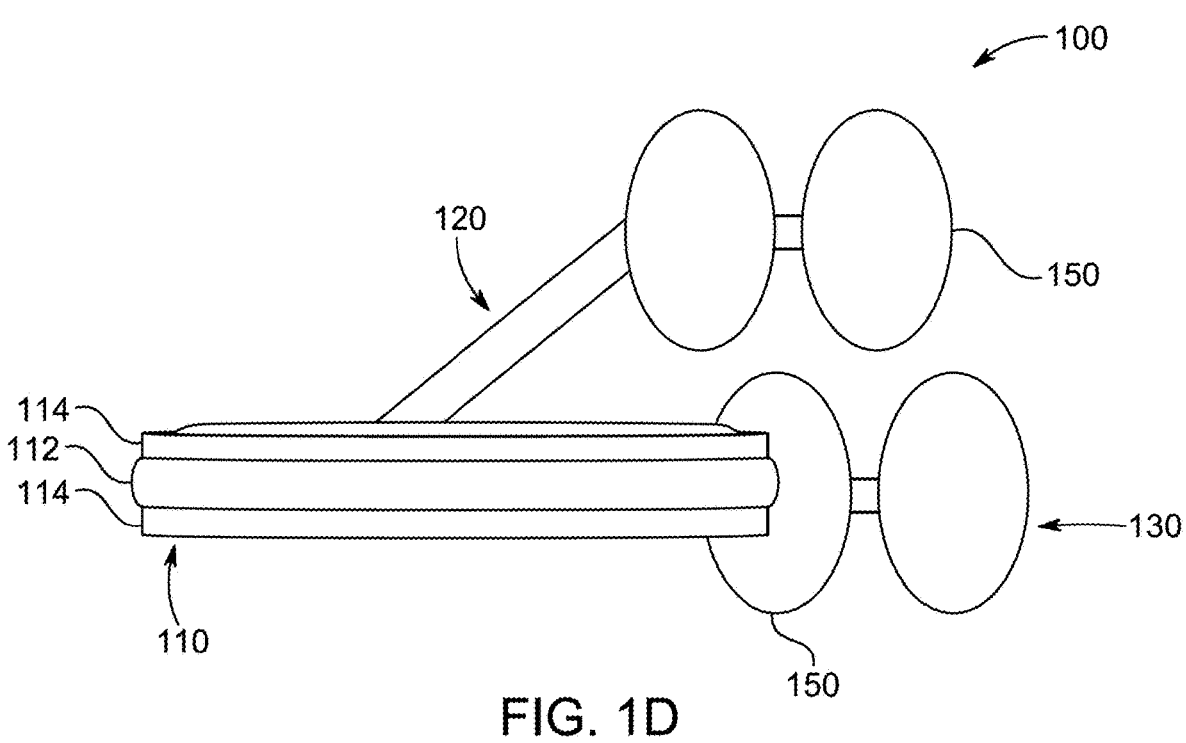
FIG. 1D is a left side view of the bone repositioning device shown in FIG. 1A, according to certain aspects of the present disclosure.
Figure 1E:
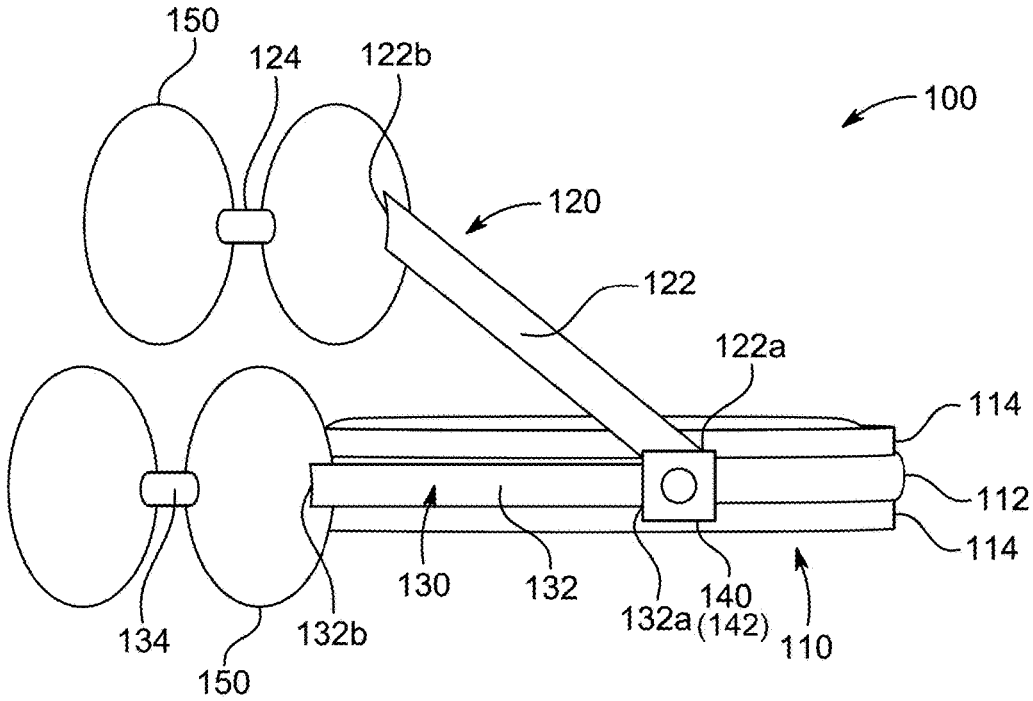
FIG. 1E is a right side view of the bone repositioning device shown in FIG. 1A, according to certain aspects of the present disclosure.

The base frame 110 serves as a foundation for the bone repositioning device 100 and is configured to be anchored to a stable bone adjacent to the bone area requiring repositioning. The base frame 110 provides a stable and uniform frame, which supports other components of the bone repositioning device 100 and ensures even distribution of loads during bone manipulation. As shown in FIG. 1A and FIG. 1B, the base frame 110 comprises a torus support 112. The term "torus support" as used herein refers to a ring-shaped or halo-shaped structure that provides a continuous and rigid foundation around the surgical site. The halo-shaped configuration of the torus support 112 offers multi-directional access for connecting the first armature 120 and the second armature 130, which facilitates simultaneous bilateral adjustments and enhances surgical precision.

The base frame 110 has a plurality of circular frames 114 on the outer surface of the torus support 112. These circular frames 114 may function as attachment points or interfaces for securing the base frame 110 to the bone. The base frame 110 is affixed to the skull or other stable bone via transcutaneous pins or screws, which are anchored into the outer cortical bone layer through strategically placed holes within the structure of the torus support 112 or the circular frames 114. These fixation points are selected to avoid critical anatomical structures while ensuring rigid support for the entire bone repositioning device 100. In some embodiments, the base frame 110 may include a plurality of holes, e.g., 2, 3, 4, 5, 6, 7, 8 holes, on the torus support 112 and/or the circular frame 114, allowing pins or screws to anchor the device 100 to a stable bone, wherein the plurality of holes are circumferentially distributed at an equal distance on the base frame 110. In some aspects, the base frame 110 has a diameter of 0.1 to 10 cm. The specific diameter of the base frame 110 may be selected based on the anatomical location and the scale of the surgical procedure.

The bone repositioning device 100 includes the first armature 120 and the second armature 130 connecting to the base frame 110. The first armature 120 and the second armature 130 are adjustable mechanical assemblies designed to connect to a movable bone segment and apply controlled forces or displacements for repositioning. Each armature is equipped with components that facilitate linear and angular adjustments, providing the surgeon with precise control over the position of the bone. The structure of the armatures 120, 130 is detailed with primary reference to the side views, such as in FIG. 1E.

Herein, the first armature 120 comprises a first shaft 122 having a first base end 122a and a first support end 122b. The first shaft 122 constitutes the primary structural element of the first armature 120. The first base end 122a is the portion of the first shaft 122 that connects to the joint 140, thereby linking the first armature 120 to the base frame 110. The first support end 122b is the distal end of the first shaft 122, which serves as a connection point for other components of the first armature 120 that interface with the bone. This arrangement facilitates the transmission of forces and movements from the joint 140 along the length of the first shaft 122. In some aspects, the first shaft 122 has a length of 0.1 to 15 cm. The length of the first shaft 122 is selected to provide adequate reach from the base frame 110 to the target bone area while maintaining structural rigidity.

The first armature 120 further comprises a second shaft 124 connecting to the first support end 122b of the first shaft 122. The second shaft 124 extends from the first shaft 122 and is the component that directly carries the dome-shaped pads 150 for contact with the bone. The connection between the second shaft 124 and the first support end 122b is configured to permit adjustments in the orientation and position of the second shaft 124 relative to the first shaft 122. This adjustability is a component of the precise alignment mechanism of the bone repositioning device 100.

In some aspects, the second shaft 124 is configured to rotate around the axis of the first shaft 122 at an angle of 10 to 350 degrees. This rotational capability allows for fine-tuning the angular position of the bone-contacting elements to match the specific anatomical contours and requirements of the surgical procedure. In some aspects, the second shaft 124 is configured to have an adjustable length. This feature, which may be implemented as a telescopic mechanism or the like, provides for controlled linear displacement of bone segments. The ability to extend or retract the second shaft 124 facilitates gradual repositioning of the bone. In some aspects, the second shaft 124 has a length of 0.1 to 5 cm, and is capable of extending to a length of 5 to 15 cm. This range of adjustment provides versatility for accommodating different anatomical dimensions and surgical requirements.

Further, the second armature 130 has a structure that corresponds to the first armature 120, providing a second point of connection and control for manipulating the movable bone segment. The presence of two armatures 120, 130 facilitates balanced force application and provides enhanced stability for complex fractures or repositioning procedures. The structure of the second armature 130 is also detailed with reference to the side views of the bone repositioning device 100, such as in FIG. 1E.

Herein, the second armature 130 comprises a third shaft 132 having a second base end 132*a* and a second support end 132*b*. The third shaft 132 serves as the main structural component of the second armature 130. The second base end 132*a* connects to the joint 140, attaching the second armature 130 to the base frame 110. The second support end 132*b* is the end of the third shaft 132 opposite the second base end 132*a* and provides a mounting point for the fourth shaft 134. This construction allows forces and adjustments originating at the joint 140 to be transmitted through the third shaft 132 to the bone contact interface. In some aspects, the third shaft 132 has a length of 0.1 to 15 cm. The length of the third shaft 132 is comparable to that of the first shaft 122, ensuring symmetrical design and balanced operation of the bone repositioning device 100.

The second armature 130 further comprises a fourth shaft 134 connecting to the second support end 132*b* of the third shaft 132. The fourth shaft 134 extends from the third shaft 132 and supports a portion of the plurality of dome-shaped pads 150. The connection between the fourth shaft 134 and the second support end 132*b* is designed to be adjustable, mirroring the functionality of the connection in the first armature 120. This adjustability permits precise positioning of the bone-contacting elements of the second armature 130.

In some aspects, the fourth shaft 134 is configured to rotate around the axis of the third shaft 132 at an angle of 10 to 350 degrees. This rotational adjustment allows the surgeon to orient the dome-shaped pads 150 on the second armature 130 to achieve optimal contact and leverage on the movable bone segment. In some aspects, the fourth shaft 134 is configured to have an adjustable length. This feature facilitates controlled linear adjustments, which is used for gradual bone repositioning. The adjustable length may be achieved through a telescopic sliding segment or a similar mechanism. In some aspects, the fourth shaft 134 has a length of 0.1 to 5 cm, and is capable of extending to a length of 5 to 15 cm. This range of extension provides the necessary adaptability for various clinical scenarios and patient anatomies.

The bone repositioning device 100 further comprises the plurality of dome-shaped pads 150. The plurality of dome-shaped pads 150 serve as the interface between the armatures of the bone repositioning device 100 and the surface of the bone to be repositioned. These components are designed as rigid, concave interface modules that are anatomically contoured to rest over selected regions of the bone, such as the cranium. Unlike suction cups, these pads are non-suction-based bone contact fixtures that rely on mechanical anchoring for secure fixation.

Figure 1F:
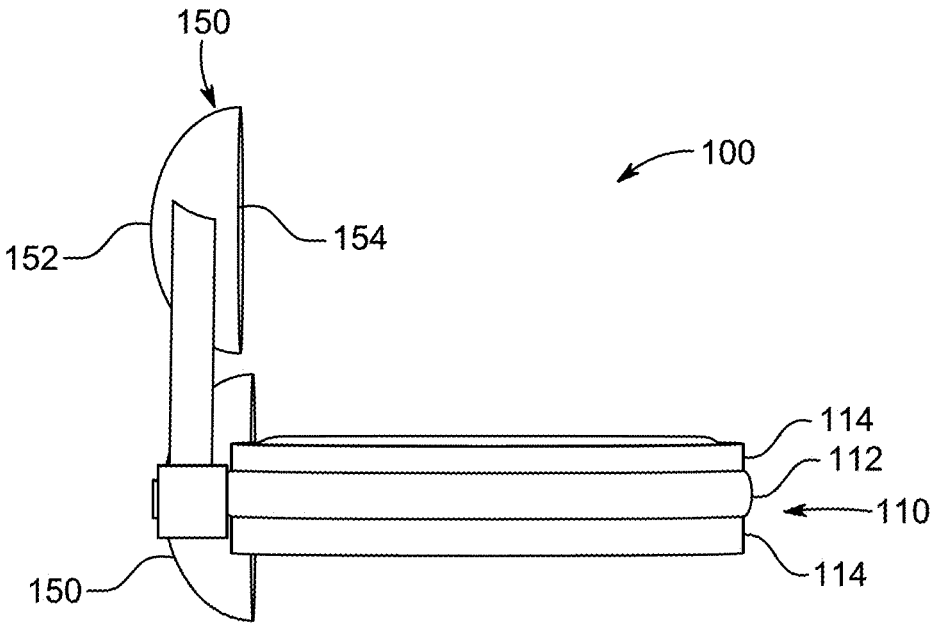
FIG. 1F is a front view of the bone repositioning device shown in FIG. 1A, according to certain aspects of the present disclosure.
Figure 1G:
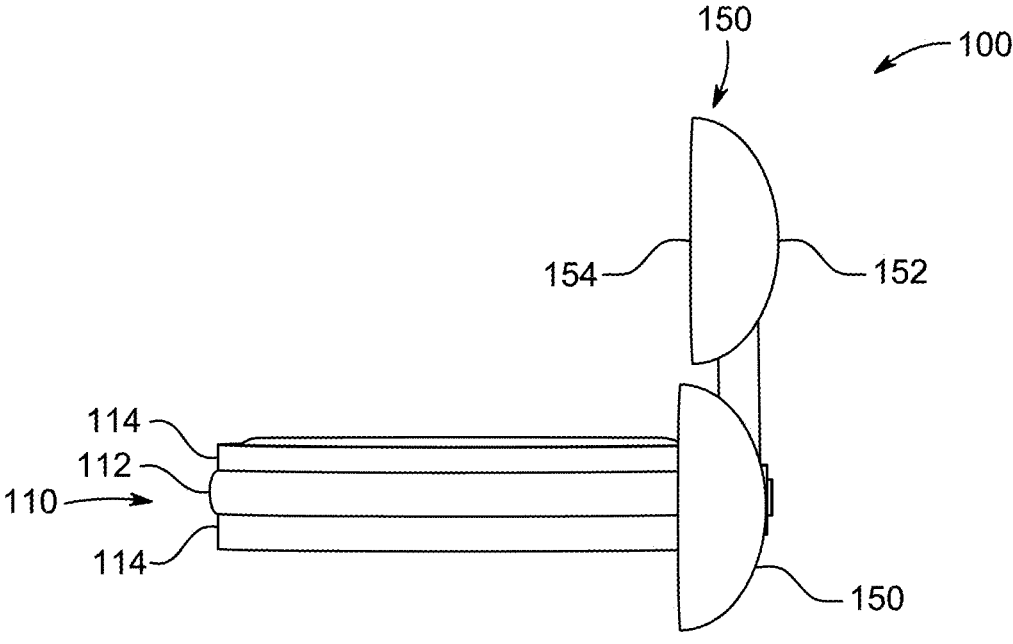
FIG. 1G is a back view of the bone repositioning device shown in FIG. 1A, according to certain aspects of the present disclosure.

As illustrated in FIGS. 1F and 1G, each of the plurality of dome-shaped pads 150 has a dome side 152 and a contact side 154. The dome side 152 is the convex outer surface of the pad, which interfaces with the shafts of the armatures. The contact side 154 is preferably a concave inner surface that is shaped to conform to the curved surface of a bone such that the contact side is in full and continuous contact with a bone surface, such as the skull. The plurality of dome-shaped pads 150 are configured to attach to a bone surface on the contact side 154. This attachment is achieved by mechanically anchoring the pads to the bone using biocompatible percutaneous screws or pins. These screws or pins are inserted through pre-formed holes or slots in the base of each pad, securing the pad directly to the outer cortical layer of the bone. This method of attachment ensures a rigid and stable connection between the bone repositioning device 100 and the movable bone segment.

The plurality of dome-shaped pads 150 are evenly distributed on the second shaft 124 and the fourth shaft 134. This distribution ensures that the forces applied for bone repositioning are spread out over a larger area, reducing stress concentration on the bone and providing stable, multi-point fixation. The arrangement of the pads on both the second shaft 124 and the fourth shaft 134 allows for a balanced and controlled manipulation of the movable bone segment from multiple points of contact. The second shaft 124 and the fourth shaft 134 pass through the plurality of dome-shaped pads 150. This configuration allows the pads to be positioned at various points along the length of the shafts, providing further adjustability to accommodate different bone sizes and fracture patterns.

In some aspects, each of the plurality of dome-shaped pads 150 has a diameter of 0.05 to 5 cm. Further, in some aspects, each of the plurality of dome-shaped pads 150 has a depth of 0.05 to 3 cm. The specific dimensions of the dome-shaped pads 150 are selected to match the scale of the target bone and the requirements of the surgical procedure, providing an appropriate contact area for effective and safe bone manipulation.

The bone repositioning device 100 further comprises the joint 140 connecting the first armature 120 and the second armature 130 at the base end to the base frame 110. The joint 140 is a mechanical connection point that links the first armature 120 and the second armature 130 to the base frame 110. As shown in views such as FIG. 1E, the joint 140 connects the first armature 120 at the first base end 122*a* and the second armature 130 at the second base end 132*a* to the base frame 110. The joint 140 serves as the central pivot and adjustment hub for the armatures, facilitating their movement relative to the stable base frame 110. This functionality is part of the precise alignment mechanism of the bone repositioning device 100.

The joint 140 is configured to allow the first armature 120 and the second armature 130 to have three degrees of freedom. This multi-axial movement capability is designed to permit a wide range of adjustments necessary for complex bone repositioning procedures. The three degrees of freedom facilitate translational and rotational adjustments of the armatures in multiple planes, providing the surgeon with the flexibility to accurately align bone fragments. The first armature 120 and the second armature 130 are configured to move around the joint 140. This movement is controlled and deliberate, guided by the surgeon to achieve the desired final position of the movable bone segment.

In some aspects, the first armature 120 and the second armature 130 are configured to have movements in forward, backward, rotational, and vertical direction around the joint 140. These specific movements correspond to the degrees of freedom provided by the joint 140. Forward and backward movements allow for adjustment along one axis, vertical movement allows for adjustment along another perpendicular axis, and rotational movement allows for angular adjustment. This combination of movements enables the precise three-dimensional positioning of the armatures and, consequently, the attached bone segment. The joint 140 may incorporate mechanisms such as a translation control unit to facilitate these movements. Such a unit may use a threaded rod or leadscrew mechanism to provide precise linear movement and fine control of bone displacement along a defined axis.

In some aspects, the joint 140 further comprises a locking system 142, configured to restrict movement of the first armature 120 and the second armature 130. The locking system 142 ensures secure fixation of the repositioned bone and all adjustable elements of the bone repositioning device 100. Once the desired alignment of the bone fragments is achieved by adjusting the armatures, the locking system 142 is engaged to freeze the position of the joint 140 and the armatures, preventing any unintended micro-movements during the healing process. This ensures that the bone heals in the correct anatomical configuration. Once engaged, the locking system 142 prevents micro-movements of the adjusted components, ensuring the bone repositioning device 100 maintains the intended anatomical configuration throughout the healing process or distraction protocol. All components of the locking system 142 are fabricated from surgical-grade, biocompatible materials, such as stainless steel or titanium alloys, selected for high durability and resistance to mechanical loads encountered during use. The design of these locking elements facilitates easy operation with standard surgical tools.

For present purposes, the locking system 142 may incorporate multiple locking mechanisms distributed across key adjustable areas to ensure secure fixation. For instance, where multi-axial angular adjustment is provided between shafts (e.g., between first shaft 122 and second shaft 124), the locking system 142 may employ rotating compression knobs or ball-and-socket tension locks to freeze the angle once achieved. For adjustable length shafts (e.g., second shaft 124, fourth shaft 134), the locking system 142 may utilize threaded clamping sleeves or split-ring locking collars to fix the length after adjustment, preventing unintended sliding or telescoping. At the central connection of the joint 140, the locking system 142 might incorporate a fine-threaded skewing screw mechanism allowing accurate rotation or angulation between the armatures, secured by a rotating torque knob or a dual-nut thread stop system. If a translation control unit is included in the joint 140, the locking system 142 may comprise a self-locking screw-based linear actuator possibly supplemented by a secondary locking screw or nut.

The locking system 142 may include an angular adjustment lock at the connection point of the shafts within each armature. For example, some of the dome-shaped pads 150 may feature a multi-axial angular adjustment mechanism, and once a desired angle is achieved, it can be locked in place using rotating compression knobs or ball-and-socket tension locks that exert controlled clamping force to freeze the joint angle. The locking system 142 may also include a telescopic rod lock for the adjustable-length shafts. After the length of a shaft, such as the second shaft 124 or fourth shaft 134, is adjusted, it can be fixed using threaded clamping sleeves or split-ring locking collars, which ensure no sliding or telescoping occurs.

The locking system 142 may further incorporate a pivot point lock at the central connection of the joint 140 where the armatures meet. This may utilize a fine-threaded skewing screw mechanism that allows for accurate rotation or angulation between the arms, followed by high-precision locking using a rotating torque knob or a dual-nut thread stop system to secure the angular relationship between the device segments. Additionally, a translation control lock may be part of the locking system 142, which may include a screw-based linear actuator that is self-locking by design to prevent back-driving, along with a secondary locking screw or nut for extra positional security. All elements of the locking system 142 are designed for high durability and resistance to mechanical loads.

In the bone repositioning device 100, adjustability is provided in the armatures themselves. As discussed, the second shaft 124 is configured to rotate around the axis of the first shaft 122 at an angle of 10 to 350 degrees; and the fourth shaft 134 is configured to rotate around the axis of the third shaft 132 an angle of 10 to 350 degrees. This extensive range of rotation for the second shaft 124 and fourth shaft 134 provides the surgeon with a high degree of control over the orientation of the dome-shaped pads 150 relative to the bone surface, which is beneficial for accommodating complex anatomical structures and achieving precise alignment. Further, the second shaft 124 and fourth shaft 134 having an adjustable length, allows for precise linear movement and controlled displacement of bone segments. This is required for procedures that require gradual repositioning of the bone over time, such as in distraction osteogenesis, or for making fine translational adjustments during a surgical procedure. These connections may incorporate a multi-axial angular adjustment mechanism. Such a mechanism facilitates fine-tuned orientation of the second shaft 124, and consequently the plurality of dome-shaped pads 150 carried thereon, relative to the bone surface.

In some aspects, the bone repositioning device 100 is made with a biocompatible material selected from the group consisting of a non-biodegradable metallic material, a bio-degradable metallic material, a non-biodegradable polymer, a bio-degradable polymer, a bioceramic material, and combinations thereof. The selection of materials is based on the requirements for strength, durability, and compatibility with human tissue. In some aspects, the bone repositioning device 100 is made with a biocompatible metallic material selected from the group consisting of titanium, a titanium alloy, stainless steel, a cobalt-chromium alloy, porous tantalum, gold, silver, magnesium, a magnesium alloy, iron, an iron alloy, zinc, a zinc alloys, and combinations thereof. These metallic materials are selected for their high strength, corrosion resistance, and established history of use in medical implants.

In other aspects, the bone repositioning device 100 is made with a biocompatible polymer selected from the group consisting of polylactic acid, polyglycolic acid, polycaprolactone, polyethylene terephthalate, polyurethanes, polyetheretherketone, polyethylene, polytetrafluoroethylene, polystyrene, polycarbonates, collagen, gelatin, chitosan, cellulose, and combinations therefore. Polymeric materials may be chosen for their lightweight properties or, in the case of bioabsorbable polymers, for their ability to degrade over time within the body, which can eliminate the need for a second surgery to remove the device. In some aspects, the bone repositioning device 100 is made with a bioceramic material selected from the group consisting of calcium phosphate cements, hydroxyapatite, tricalcium phosphate, biphasic calcium phosphate, bioactive glass, and combinations thereof. Bioceramic materials may be used for their bone-integrating properties. In some aspects, the bone repositioning device 100 is made with a biodegradable material having a degradation period of 14 to 1000 days.

Figure 2:
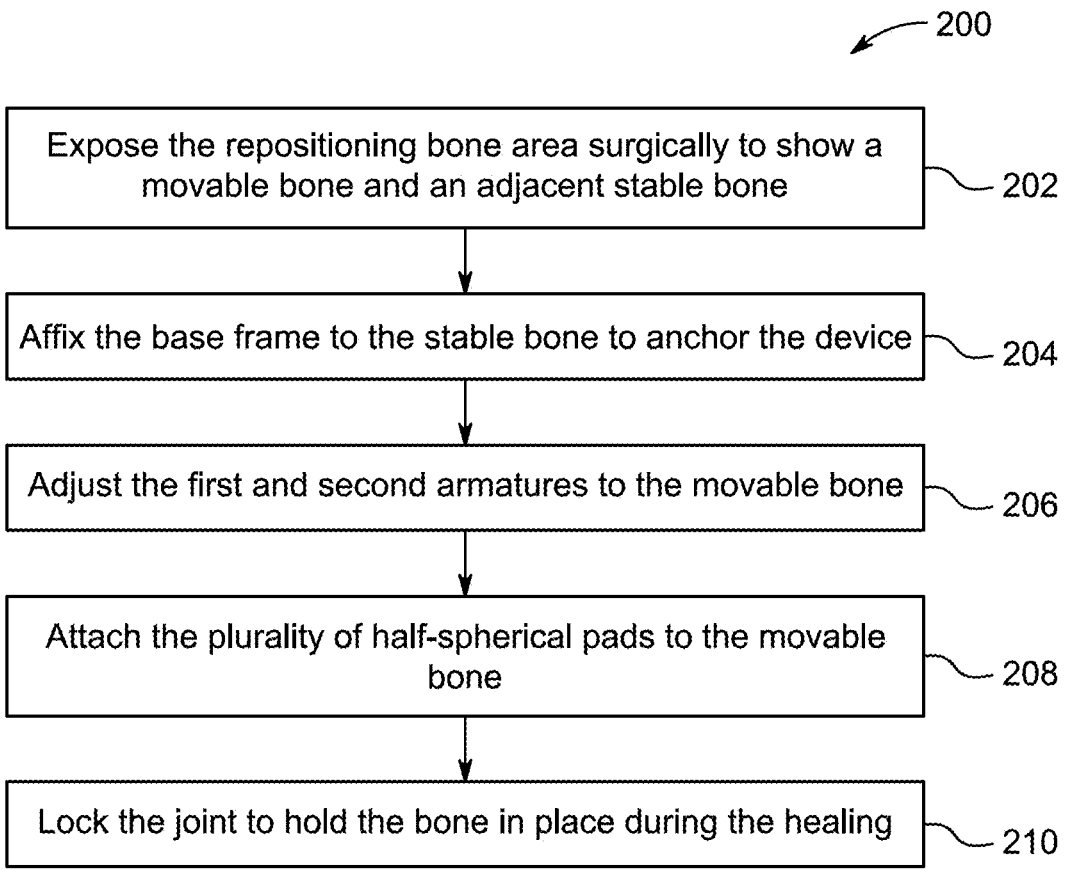
FIG. 2 is a flowchart illustrating a method of use for the bone repositioning device, according to certain aspects of the present disclosure.

Referring now to FIG. 2, a flowchart illustrating a method 200 of repositioning and healing a bone using the bone repositioning device 100 is shown. The method 200 outlines a sequence of steps performed during a surgical procedure to utilize the bone repositioning device 100 for achieving accurate alignment and stable fixation of a movable bone segment relative to an adjacent stable bone. The method 200 involves preparation of the surgical site, application and adjustment of the bone repositioning device 100, and securing the device to maintain the desired bone position during the healing phase. Each step of the method 200 corresponds to a specific action taken by the surgeon to employ the features of the bone repositioning device 100 effectively At step 202, the method 200 includes exposing the repositioning bone area surgically to show a movable bone and an adjacent stable bone. This initial step prepares the surgical site by providing clear access to the bone segments that require manipulation and stabilization. At step 204, the method 200 includes affixing the base frame 110 to the stable bone to anchor the device. This is a foundational step where the base frame 110 is securely attached to a non-moving part of the bone structure, providing a solid anchor point for the rest of the bone repositioning device 100. In some aspects, the affixing is achieved using one or more cortical screws.

At step 206, the method 200 includes adjusting the first armature 120 and the second armature 130 to the movable bone. In this step, the surgeon manipulates the various adjustable components of the armatures 120, 130, such as the shafts and the joint 140, to bring the dome-shaped pads 150 into the correct position relative to the movable bone fragment. At step 208, the method 200 includes attaching the plurality of half-spherical pads (i.e., the plurality of dome-shaped pads 150) to the movable bone. Once properly positioned, the pads 150 are secured to the bone. In some aspects, the attaching further comprises mounting the plurality of half-spherical pads (dome-shaped pads 150) to the movable bone with screws, glue, or suction. In some examples, the plurality of dome-shaped pads 150 are mounted to the movable bone using biocompatible percutaneous screws or pins inserted through pre-formed holes or slots in the pads 150. Securing the pads with screws provides a rigid mechanical connection.

At step 210, the method 200 includes locking the joint 140 to hold the bone in place during the healing. After the movable bone has been repositioned to the desired anatomical alignment, the surgeon engages the locking system 142 of the joint 140. This action freezes all adjustable components of the bone repositioning device 100, ensuring that the bone fragments remain stable and immobile throughout the healing process. In some aspects, the method 200 further comprises removing the device after the healing. That is, if the bone repositioning device 100 is made from non-biodegradable materials, a subsequent procedure may be performed to remove the device once the bone has healed sufficiently.

The bone repositioning device 100 is versatile in its application. In some aspects, the bone repositioning device 100 is used in at least one bone selected from the group consisting of skull, jaw bone, collar bone, shoulder blade, sternum, humerus, radius, ulna, spine, pelvis, sacrum, femur, patella, tibia, and fibula. The customizable and adaptive features of the device make it suitable for a wide range of anatomical locations and fracture types, from craniofacial surgery to orthopedic procedures involving long bones or complex joints.

The bone repositioning device 100 provides the significant configuration for bone manipulation by integrating the stable base frame 110 with the first armature 120 and the second armature 130. The functional relationship between the base frame 110, which comprises the torus support 112, and the armatures is established through the joint 140 that is configured to allow three degrees of freedom. This arrangement, wherein the first armature 120 and the second armature 130 are configured to move around the joint 140, facilitates precise control over the positioning of the movable bone. The use of the plurality of dome-shaped pads 150, which are evenly distributed on the second shaft 124 and the fourth shaft 134, creates the distributed and stable interface for attachment to the bone surface on the contact side 154 of the plurality of dome-shaped pads 150.

The bone repositioning device 100 offers advantages in surgical procedures by providing extensive adjustability and secure fixation. Applications for the bone repositioning device 100 include, but are not limited to, craniofacial repositioning, stabilization of cranial fractures, and distraction osteogenesis procedures involving the skull, where precise bone manipulation and stabilization are required. The configuration of the joint 140 allows the first armature 120 and the second armature 130 to have movements in forward, backward, rotational, and vertical directions, which enables multi-planar adjustments to the bone's position. Furthermore, the capacity for the second shaft 124 to rotate around the axis of the first shaft 122 and the fourth shaft 134 to rotate around the axis of the third shaft 132, combined with the adjustable length of the second shaft 124 and the fourth shaft 134, provides fine control over the final placement of the bone segment. After the desired alignment is achieved, the locking system 142 of the joint 140 is configured to restrict movement of the first armature 120 and the second armature 130, ensuring the repositioned bone is held securely in place to facilitate healing.

Numerous modifications and variations of the present disclosure are possible in light of the above teachings. It is therefore to be understood that within the scope of the appended claims, the invention may be practiced otherwise than as specifically described herein.

The invention claimed is:

1. A bone repositioning device, comprising:
a base frame comprising a torus support having a plurality of circular frames on an outer surface of the torus support;
a first armature and a second armature connecting to the base frame,
wherein the first armature comprises:
    a first shaft having a first base end and a first support end; and
    a second shaft connecting to the first support end of the first shaft;
wherein the second armature comprises:
    a third shaft having a second base end and a second support end;
    a fourth shaft connecting to the second support end of the third shaft; and
a plurality of dome-shaped pads having a dome side and a contact side,
wherein the plurality of dome-shaped pads are configured to attach to a bone surface on the contact side;
wherein the plurality of dome-shaped pads are evenly distributed on the second shaft and the fourth shaft; and
wherein the second shaft and the fourth shaft pass through the plurality of dome-shaped pads;
a joint connecting the first armature and the second armature at the base end to the base frame, configured to allow the first armature and the second armature to have three degrees of freedom,
wherein the first armature and the second armature are configured to move around the joint.

2. The bone reposition device of claim 1, wherein the joint further comprises a locking system, configured to restrict movement of the first armature and the second armature.

3. The bone reposition device of claim 1, wherein the first armature and the second armature are configured to have movements in forward, backward, rotational, and vertical direction around the joint.

4. The bone reposition device of claim 1, wherein the second shaft is configured to rotate around the axis of the first shaft at an angle of 10 to 350 degrees; and wherein the fourth shaft is configured to rotate around the axis of the third shaft an angle of 10 to 350 degrees.

5. The bone reposition device of claim 1, wherein the second shaft and fourth shaft are configured to have an adjustable length.

6. The bone reposition device of claim 1, wherein the base frame has a diameter of 0.1 to 10 cm.

7. The bone reposition device of claim 1, wherein the first shaft and the third shaft each has a length of 0.1 to 15 cm.

8. The bone reposition device of claim 1, wherein the second shaft and the fourth shaft each has a length of 0.1 to 5 cm, and is capable of extending to a length of 5 to 15 cm.

9. The bone reposition device of claim 1, wherein each of the plurality of dome-shaped pads has a diameter of 0.05 to 5 cm.

10. The bone reposition device of claim 1, wherein each of the plurality of dome-shaped pads has a depth of 0.05 to 3 cm.

11. The bone reposition device of claim 1, which is made with a biocompatible material selected from the group consisting of a non-biodegradable metallic material, a biodegradable metallic material, a non-biodegradable polymer, a bio-degradable polymer, a bioceramic material, and combinations thereof.

12. The bone reposition device of claim 1, which is made with a biocompatible metallic material selected from the group consisting of titanium, a titanium alloy, stainless steel, a cobalt-chromium alloy, porous tantalum, gold, silver, magnesium, a magnesium alloy, iron, an iron alloy, zinc, a zinc alloys, and combinations thereof.

13. The bone reposition device of claim 1, which is made with a biocompatible polymer selected from the group consisting of polylactic acid, polyglycolic acid, polycaprolactone, polyethylene terephthalate, polyurethanes, polyetheretherketone, polyethylene, polytetrafluoroethylene, polystyrene, polycarbonates, collagen, gelatin, chitosan, cellulose, and combinations therefore.

14. The bone reposition device of claim 1, which is made with a bioceramic material selected from the group consisting of calcium phosphate cements, hydroxyapatite, tricalcium phosphate, biphasic calcium phosphate, bioactive glass, and combinations thereof.

15. A method of repositioning and healing a bone using the bone reposition device in claim 1, comprising:

exposing the repositioning bone area surgically to show a movable bone and an adjacent stable bone;

affixing the base frame to the stable bone to anchor the device;

adjusting the first and second armatures to the movable bone;

attaching the plurality of half-spherical pads to the movable bone; and locking the joint to hold the bone in place during the healing.

16. The method of claim 15, further comprises:

removing the device after the healing.

17. The method of claim 15, wherein the affixing is achieved using one or more cortical screws.

18. The method of claim 15, wherein the attaching further comprises:

mounting the plurality of half-spherical pads to the movable bone with screws, glue, or suction.

19. The bone reposition device of claim 1, which is made with a biodegradable material having a degradation period of 14 to 1000 days.

20. The bone reposition device of claim 1, which is used in at least one bone selected from the group consisting of skull, jaw bone, collar bone, shoulder blade, sternum, humerus, radius, ulna, spine, pelvis, sacrum, femur, patella, tibia, and fibula.

*  *  *  *  *